(12) United States Patent
Mueller et al.

(10) Patent No.: US 9,458,494 B2
(45) Date of Patent: Oct. 4, 2016

(54) EXTRACTION OF NUCLEIC ACIDS FROM WAX-EMBEDDED SAMPLES

(75) Inventors: Markus Mueller, Hilden (DE); Thorsten Singer, Hilden (DE); Esther Rosenberg, Hilden (DE); Joerg Hucklenbroich, Hilden (DE)

(73) Assignee: QIAGEN GmbH, Hilden (DE)

( * ) Notice: Subject to any disclaimer, the term of this patent is extended or adjusted under 35 U.S.C. 154(b) by 436 days.

(21) Appl. No.: 13/703,205

(22) PCT Filed: Jun. 14, 2011

(86) PCT No.: PCT/EP2011/059784
§ 371 (c)(1),
(2), (4) Date: Jul. 8, 2013

(87) PCT Pub. No.: WO2011/157683
PCT Pub. Date: Dec. 22, 2011

(65) Prior Publication Data
US 2013/0280787 A1    Oct. 24, 2013

(30) Foreign Application Priority Data
Jun. 14, 2010   (EP) ................................. 10165799

(51) Int. Cl.
*C12N 15/10* (2006.01)
*C12Q 1/68* (2006.01)
*G06F 19/20* (2011.01)

(52) U.S. Cl.
CPC ......... *C12Q 1/6806* (2013.01); *C12N 15/1003* (2013.01)

(58) Field of Classification Search
USPC .................. 435/270, 6.12; 506/9; 536/25.41; 702/19
IPC ............. C12N 15/10; C12Q 1/68; G06F 19/20
See application file for complete search history.

(56) References Cited

U.S. PATENT DOCUMENTS

| | | | |
|---|---|---|---|
| 4,035,234 A | 7/1977 | Schutt | |
| 5,393,672 A | 2/1995 | Ness et al. | |
| 5,654,179 A | 8/1997 | Lin | |
| 5,817,765 A | 10/1998 | Isaksson et al. | |
| 5,877,141 A | 3/1999 | Gabriel et al. | |
| 2006/0084130 A1 | 4/2006 | Deslys et al. | |
| 2006/0188892 A1 | 8/2006 | Latham et al. | |
| 2009/0232808 A1 | 9/2009 | Priest et al. | |
| 2010/0331534 A1 | 12/2010 | Khan et al. | |
| 2013/0172539 A1 | 7/2013 | Miyagi et al. | |

FOREIGN PATENT DOCUMENTS

| | | | |
|---|---|---|---|
| EP | 0 261 956 A2 | 3/1988 | |
| EP | 1 245 674 A2 | 10/2002 | |
| EP | 1 743 939 A2 | 1/2007 | |
| EP | 2 270 151 A1 | 1/2011 | |
| WO | 95/24498 A1 | 9/1995 | |
| WO | 96/00228 A1 | 1/1996 | |
| WO | 99/16869 A1 | 4/1999 | |
| WO | 01/94574 A2 | 12/2001 | |
| WO | 2006/130632 A2 | 12/2006 | |
| WO | 2007/050327 A2 | 5/2007 | |
| WO | 2009/127350 A1 | 10/2009 | |

OTHER PUBLICATIONS

BioGenex "Safety Data Sheet—EZ Dewax Solution, Ready to Use," XP-002602420, 90 pages (Oct. 30, 2003).
Buesa et al., "Histology without xylene," Annals of Diagnostic Pathology 13:246-256 (2009).
Epicentre Biotechnologies—SoilMaster™ DNA Extraction Kit, Cat Nos. SM02050, SM02005, SC04350, and SR04350, XP002604830, Retrieved from the Internet:URL:http://www.epibio.com/pdfteehlit/178p10310, (Retrieved on Jun. 9, 2010) 4 pages (Mar. 29, 2010).
Forcic et al., "Purification of genomic DNA by short monolithic columns," *Journal of Chromatography A* 1065:115-120 (2005).
"Fungus," Wikipedia.com (accessed Jun. 3, 2013) (28 pages).
Hanselle et al., "Isolation of genomic DNA from buccal swabs for forensic analysis, using fully automated silica-membrane purification technology," *Legal Medicine* 5:S145-S149 (2003).
Heilig et al., "Large-Scale Preparation of Plasmid DNA," *Current Protocols in Molecular Biology* Chapter 1, Units 1.7.1-1.7.16 (1998).
"How Many Species of Bacteria Are There?" wisegeek.com (accessed Sep. 23, 2011) (2 pages).
Macherey-Nagel, Viral DNA/RNA Isolation, User Manual, NucleoSpin® & Virus, Nucleospin® & Virus Core Kit, 30 pages (Mar. 2010).
"Mammal," Wikipedia.com (accessed Sep. 22, 2011) (17 pages).
"Murinae," Wikipedia.com (accessed Mar. 18, 2013) (21 pages).
Okello et al., "Comparison of methods in the recovery of nucleic acids from archival formalin-fixed paraffin-embedded autopsy tissues," *Analytical Biochemistry* 400:110-117 (2010).
"Plant," Wikipedia.com (accessed Mar. 8, 2013) (12 pages).
Prodelalova et al., "Isolation of genomic DNA using magnetic cobalt ferrite and silica particles," *Journal of Chromatography A* 1056:43-48 (2004).
Qiagen, QIAamp® DNA Stool Mini Kit Handbook, XP002604829, 40 pages (Aug. 2001).
Qiagen, User-Developed Protocol: Purification of viral RNA and DNA from 1000 µl of plasma, serum, and cell-free body fluids using the QIAmp® MinElute® Virus Vacuum Kit, XP002587174, 6 pages (Jun. 2004).

(Continued)

*Primary Examiner* — Debbie K Ware
*Assistant Examiner* — Kailash C Srivastava
(74) *Attorney, Agent, or Firm* — Seed Intellectual Property Law Group PLLC (57) ABSTRACT

Provided is a method for extracting nucleic acids from a wax-embedded sample, and use of particular solvents for removing wax from a wax-embedded sample for extracting, isolating and/or purifying nucleic acids from a crosslinked wax-embedded sample.

30 Claims, 3 Drawing Sheets

(56) References Cited

OTHER PUBLICATIONS

Sambrook et al., (eds.). Molecular Cloning: A Laboratory Manual: Third Edition-vol. 1, Cold Spring Harbor Laboratory Press, New York, "Protocol 8: Purification of Plasmid DNA by Precipitation with Polyethylene Glycol," 8 pages (2001).

USB Corp., PrepEase® Tissue & Cells DNA Spin Kit, Product Nos. 78860, 78861, 78862, Brief Protocol XP002587173, 2 pages (2008).

"Virus," Wikipedia.com (accessed Nov. 24, 2012).

Zhou et al., "DNA Recovery from Soils of Diverse Composition," *Applied and Environmental Microbiology*, 62(2):316-322 (Feb. 1996).

EXTRACTION OF NUCLEIC ACIDS FROM WAX-EMBEDDED SAMPLES

The present invention relates to a method for extracting nucleic acids from a wax-embedded sample, the use of specific solvents for removing wax from a wax-embedded sample in a method for extracting, isolating and/or purifying nucleic acids from a cross linked wax-embedded sample as well as to a kit for extracting, isolating and/or purifying nucleic acids from a wax-embedded sample.

On removal of biological material from a living organism, e.g. a tissue, a fragment thereof or isolated cells, the latter die after a short time unless usual measures are taken, such as, for instance, incubation in nutrient media. Cells which have died moreover rapidly undergo initial autolytic-fermentative and then bacterial decomposition, so that the original cell-in-tissue structures are destroyed. In consequence it is necessary to fix the removed biological sample in order to suppress its decomposition if a histological examination of the sample is envisaged. By means of fixation it is intended to substantially preserve the biological structures in a life-like fashion, so that "real assessment" is possible. A further advantage of fixation is the fact that the specimens can be stored as documents for a long time. Furthermore, many morphological investigations are only possible on the basis of fixed material.

Fixation usually is achieved using precipitating or cross-linking compounds such as acids, alcohols, ketones, or aldehydes, in particular formaldehyde (commonly employed in the form of either a 4-10 wt.-% or a 35 wt.-% aqueous solution, both referred to as "formalin"), commonly followed by a step of embedding the fixed material in a wax, usually paraffin (so-called "formalin-fixed, paraffin-embedded" (FFPE) material). The main purpose of the embedding medium is to permit the specimens to be sectioned and mounted in the natural state for microscopic and/or histochemical applications. For many applications it is however necessary or at least advantageous to remove the embedding medium from the sample, for example prior to histological staining of the sample.

Traditionally, deparaffinization involves the use of aromatic solvents such as toluene and, in particular, xylene. Typically, a fresh slice or a microscope slide-mounted specimen is immersed in a xylene bath until the paraffin is solubilized. In subsequent steps the deparaffinized specimen is washed by a series of alcohol solutions of decreasing alcohol concentration to remove xylene prior to a final wash using water, in order to make the sample accessible for aqueous reactant/reagent solutions, such as for example lysis buffers or staining solutions. Xylene, however, is a flammable, volatile and toxic organic solvent. For this reason, considerable efforts have been made during the past years to replace xylene with less toxic deparaffinization agents. Examples for xylene replacements in histochemical applications include terpene oils, such as d-limonene, isoparaffinic hydrocarbons or an aqueous dishwashing soap solution (R. J. Buesa, M. V. Peshov, *Annals of Diagnostic Pathology* 2009, 13, 246-256).

Several of these deparaffinization agents perform equal to xylene with regard to the removal of wax while being less or even nontoxic. However, a series of alcohol washes is still required in many cases in order to remove the solvent/deparaffinization agent prior to a water wash in order to achieve compatibility with most types of immunohistochemical staining. With advances in biomolecular techniques, not only the light microscopic inspection of wax-embedded samples, but also analysis of nucleic acids, both DNA and RNA, recovered from wax-embedded samples, in particular from FFPE samples, has been becoming increasingly important. Nucleic acids recovered from such samples may subsequently be analyzed using highly sensitive techniques such as for example polymerase chain reaction (PCR). If however, the extraction of nucleic acids from a wax-embedded sample is envisaged instead of or in addition to immunohistochemical staining, it is very important that the deparaffinization agents either do not interfere in any subsequent step of concentrating, purifying, isolating and/or analyzing the nucleic acids or that said agents may be completely removed from the sample after deparaffinization.

For the recovery of nucleic acids from FFPE samples, said samples are usually dewaxed using xylene and washed a number of times with alcohol solutions of decreasing alcohol concentrations as well, before being lysed in an appropriate digestion buffer. In subsequent steps nucleic acids are usually isolated from these buffers using organic extraction methods such as phenol/chloroform extraction and optionally further concentrated by precipitation using for example ethanol or isopropanol.

If a chaotropic digestion buffer is used, comprising for example guanidinium thiocyanate, or, alternatively, a chaotrope is added to the sample after the digestion/lysis step, the nucleic acids may also be isolated by means of a solid phase selectively binding nucleic acids, such as for example a silica-membrane or glass beads, thus avoiding the aforementioned liquid/liquid extraction procedures using toxic solvents. On the other hand, chaotropic substances are regarded as being toxic as well.

In order to minimize the amount of toxic substances as well as the number of washing steps, several commercially available kits for the isolation of nucleic acids, including DNA and RNA, have been developed, most of them employing xylene as a deparaffinization agent, even though kits comprising for examples terpenes as a deparaffinization agent are available as well (J. B. A. Okello *Analytical Biochemistry* 2010, 400 (1), 110-117). Another approach is used in the commercially available wax-free paraffin sample preparation kit from TrimGen (Sparks, Md., USA). After removing the wax using a proprietary solution, a special resin and an enzyme mix are added to the sample. The enzyme mix digests the sample, while potential PCR inhibitors are bound to the resin, which can be easily removed form the sample prior to amplification by PCR.

While this kit may give good results in PCR based amplification of nucleic acids recovered from FFPE tissues, the method may not be suitable for other subsequent analysis procedures. In addition, the resin is adapted to the specific components present in the digestion mixture and the dewaxing solution. Hence, the kit cannot be used in combination with any lysing buffer.

The problem to be solved by the present invention therefore was to provide a method for extracting nucleic acids from a wax-embedded sample which neither requires toxic deparaffinization agents, laborious washing steps nor resins specifically adapted to capture contaminants or PCR-inhibitors from the sample.

This object is met by the method of the present invention. It has surprisingly been found, that lysis of deparaffinized former wax-embedded samples can be accomplished in a bi- or multi-phasic system still comprising the wax-solubilizing agent and the solubilized wax without compromising the lysis result. Accordingly, neither laborious washing steps nor resins for capturing contaminants are necessary.

Thus, the present invention provides a method for extracting nucleic acids from a wax-embedded sample, comprising the steps of:

1. contacting the sample with a wax-solubilizing agent comprising at least one organic solvent immiscible with water,
2. optionally incubating the mixture obtained in step 1,
3. adding an aqueous lysis buffer to the mixture still comprising the wax-solubilizing agent,
4. incubating the mixture obtained in step 3 to obtain a bi- or multi-phasic mixture, comprising at least an organic phase, said organic phase essentially comprising the dissolved wax and the wax-solubilizing agent, and an aqueous phase, said aqueous phase comprising the nucleic acids, wherein steps 1 and 3 may as well be carried out as one combined step if step 2 is omitted.

The method furthermore can comprise as optional steps:

5. separating the organic phase from the aqueous phase and/or
6. isolating and/or purifying the nucleic acids from the aqueous phase.

In terms of the present invention, the term "wax-embedded sample" comprises any biological sample embedded in a wax for example for histochemical or further chemical and/or biological analysis. Such a wax usually consists of a complex mixture of higher hydrocarbons and may include further components such as esters of higher fatty acids and/or glycols and the like. The wax may be of natural and/or synthetic origin and may additionally contain additives enhancing its sample-embedding properties such as for example DMSO or higher polyolefins. Preferably, the wax may represent paraffin, being a mixture of primarily saturated hydrocarbons solid at room temperature, which typically is prepared by distillation of petroleum. Independently of which type of paraffin is used, so-called high or low melting paraffin or a mixture thereof, the sample may be processed using the method and/or the kit of the present invention. Optionally the paraffin wax may contain additives, known in the state of the art, e.g. for improving particular characteristics of the wax, such as for example small amounts of organic polymers or DMSO.

Preferably, the sample may be a formalin-fixed paraffin-embedded sample, wherein the biological sample has been fixed using formaldehyde prior to the step of being embedded in paraffin. The biological sample may be a whole organism, a part of an organism, in particular a tissue fragment or a tissue section, originating from humans, animals or plants, or microorganisms such as for example bacteria, viruses or fungi. Embedded cells isolated from cell cultures may be used as well.

As a lysis buffer (step 3) any aqueous solution may be used which is able to lyse/destroy the cells in a cell-containing material, thus releasing the nucleic acids into solution without destroying the nucleic acids to be isolated. Many aqueous digestion buffers are known from the state of the art which can be used in the method of the present invention. If the embedded sample is a fixed sample, for example a formalin fixed sample, said digestion buffer may contain additional components known in the state of the art for reducing the number of crosslinks in the sample. However, the presence of such additional components in the lysis buffer is not mandatory, as the crosslink may be efficiently removed during incubation according to step 4, even in the absence of compounds for reducing the number of crosslinks, if an incubation temperature of about 90° C. is applied.

As these lysis buffers in general are applied to a sample in the form of an aqueous solution, after lysis a multi-phasic mixture is obtained which comprises at least one organic phase, said organic phase essentially comprising the dissolved wax and the wax-solubilizing agent, and an aqueous phase, which comprises the nucleic acids (as well as for example further cell components). In most cases, the multi-phasic mixture is a biphasic mixture comprising exactly one organic phase and exactly one aqueous phase. It is, however, for example possible to carry out the lysis step in the presence of a solid phase as well (under the proviso that the solid phase is not adapted to catch PCR inhibiting compounds from the sample), in which case the mixture may be regarded as a triphasic mixture. As well a kind of "triphasic" mixture may be observed immediately after thoroughly mixing a liquid aqueous phase and a liquid organic phase, comprising the former two phases and an intermediate "phase", formed by an emulsion of said former two phases, which usually separates very quickly once mixing is stopped. In addition, depending upon the compounds present in the lysis buffer, its pH and temperature, one or more components of the sample may precipitate from solution, forming a (further) solid phase.

After incubating the mixture according to step 4, the organic phase may optionally be separated from the aqueous phase in step 5. In addition a step of isolating and/or purifying the nucleic acids from the aqueous phase may be comprised in the method of the present invention (step 6).

A great advantage of the method of the present invention is the fact that no toxic chemicals are needed for dewaxing the sample. Furthermore no laborious washing steps or specifically adapted resins are necessary to separate the dissolved wax from the sample. In addition, the lysis buffer used in step 3 as well as any further reagents and means used in the optional step of isolating and/or purifying the nucleic acids from the aqueous phase according to step 6 may be almost freely selectable from a wide range of methods and/or means, which means that the method can be specifically adapted to a sample's particular requirements.

The wax-solubilizing agent preferably may be non-toxic and may comprise at least one organic solvent/compound immiscible with the water. The wax-solubilizing agent may be liquid, at least for the moment of contacting it with the sample. Preferably said solvent may be selected from the group comprising linear, branched and cyclic $C_{10}$-$C_{16}$ alkanes, or mixtures thereof, more preferably selected from the group comprising $C_{13}$-$C_{16}$ alkanes, or mixtures thereof, and most preferably represents tetradecane, pentadecane or hexadecane. The melting point of any solvent applied to the wax-embedded sample for dewaxing, either in a pure form or as a mixture of solvents, respectively, preferably is below room temperature ($23\pm2°$ C.). Furthermore, said solvent or mixture of solvents should neither be soluble in water, i.e. it should have a solubility in water of less than 0.01% (w/w), nor should it be miscible with water, i.e. it should not form an homogeneous solution with water upon mixing. Herein, the term "pure form" refers to a solvent applied to the wax-embedded sample in order to dissolve the wax without being diluted previously and/or mixed with other solvents. It does however not refer to a particular purity grade with respect to the presence of further compounds which do not represent a solvent. If a solvent is applied to the sample in a pure form it preferably has a melting point below room temperature. "Solvents" having a melting point above room temperature may, however, be applied to the wax-embedded sample, if they are present in a mixture of solvents, which is liquid at room temperature ($23\pm2°$ C.).

Preferably, the solvent or the mixture of solvents has/have a boiling point above 150° C., more preferably above 200°

C. and most preferably above 250° C. By choosing a wax-solubilizing agent having a boiling point above 150° C. it can be easily ensured that the sample's paraffin once liquefied stays in the liquid state and does not harden again due to an unintended evaporation of the wax-solubilizing agent. In addition, it has been found that the above mentioned organic solvents or mixtures thereof in general have a very low tendency for forming stable emulsions, with the aqueous phase obtained after adding the lysis buffer according to step 3, surprisingly even in the presence of detergents like SDS, which is in contrast to the behaviour of for example lower alkanes, such as hexane or heptane. In addition, all of the above solvents are able to dissolve the solid paraffins within a few seconds or at most a few minutes (preferably of from about 15 seconds to about 15 minutes) at room temperature.

In order to facilitate optical detection of the interface between the aqueous and the organic phase, a dye/a colorant may be comprised in the wax-solubilizing agent which is soluble in said wax-solubilizing agent, but insoluble in water, such as for instance anthraquinone solvent dyes being insoluble in water, e.g. 1,4-bis[(4-methylphenyl)amino]-9,10-anthracenedione, commercially available as "oil green". For example, an amount as small as about 1 mg of "oil green" in about 30 ml of the wax-solubilizing agent, e.g. hexadecane, equalling approximately 0.003% (w/v), is enough to impart an intense colour to the organic phase, while the colour of the aqueous phase remains unchanged, which significantly facilitates phase separation.

The step of incubating the mixture of the wax-solubilizing agent in the wax-embedded sample according to step 2 may be carried out at a temperature in the range of from 15 to 85° C., preferably of from 20 to 55° C., more preferably of from room temperature to 35° C. and most preferably at room temperature. If this incubation step is carried out, it may preferably last from 1 second to 3 hours, more preferably from 10 seconds to 1 hour, even more preferably from 20 seconds to 30 minutes and most preferably from 30 seconds to 5 minutes. As well, the wax-solubilizing agent and the aqueous lysis buffer may be applied to the sample simultaneously or "almost simultaneously", i.e. one immediately after the other, that is the dewaxing agent immediately after the lysis buffer or vice versa. In this case, optional step 2 of the method of the present invention is omitted and steps 1 and 3 are carried out simultaneously or "almost simultaneously".

In the method of the present invention it is particularly advantageous that the embedding medium can be removed from the sample very quickly and in an (almost) quantitatively manner at low temperatures, even if an aqueous lysis buffer is added to the sample simultaneously with the wax-solubilizing agent or "almost simultaneously". In consequence, there is no need for laborious and time-consuming dewaxing and phase separating steps prior to lysis.

Thus, in contrast to several methods known from the state of the art no elevated temperatures and/or long incubation times are needed for removing the wax which may have a negative impact on the quality and yield of the nucleic acids, in particular if nucleic acid-digesting enzymes are present in the sample, such as RNases and DNases, which have not (yet) been inactivated by a proteinase. The removal of paraffin prior to or simultaneously with the lysis also shortens the required lysis time, as the aqueous lysis buffer can penetrate a deparaffinized sample more quickly and efficiently than an embedded one, i.e. a shorter lysis time and/or a lower lysis temperature may be applied.

It is, however, not necessary to incubate the sample in contact with the wax-solubilizing agent prior to the addition of an aqueous lysis buffer. As well the wax-solubilizing agent and the aqueous lysis buffer may be added to the sample simultaneously. In this case, the sample preferably is mixed to ensure a thorough contacting of the phases, for example by vortexing, shaking on a laboratory shaker, pipetting up and down etc., without being limited to these. Additional compounds, such as a protease, may be added as well.

The method of the present invention can be used in combination with a wide range of lysis buffer and lysis protocols known from the state of the art, such as for example buffer ATL comprised in the QIAamp FFPE kit, buffer P1 comprised in the QIAsymphony DNA kit (both available from QIAGEN, Hilden, Germany), or buffer PBS. The lysis buffer may for example comprise a buffering agent, preferably selected from the group comprising Tris, Mops, Mes, Hepes, borates, phosphates and carbonates and at least a detergent, preferably selected from the group comprising nonionic, anionic, cationic and zwitterionic detergents, or a mixture thereof. More preferred the detergents are selected from anionic or zwitterionic detergents. Most preferably the lysis buffer may comprise anionic detergents, most preferably sodium dodecyl sulfate. Furthermore nonionic surfactants, such as substituted phenol or sugar polyethoxylates, commercially available for instance as Triton X-114 (Dow Chemical Co., Midland, Mich., USA), Triton X-100 (Dow Chemical Co., Midland, Mich., USA) or Tween 20 (Merck, Darmstadt, Germany) may be used, as well as cationic surfactants, such as quaternary ammonium surfactants, e.g. cetyltrimethylammonium bromide (CTAB) or tetradecyl trimethylammonium bromide (TTAB).

The lysis buffer may comprise one or more additional substances, preferably selected from the group comprising chelating agents, reducing agents, inorganic salts, such as ammonium sulphate, pH-indicators, and stabilizers such as sodium azide. Preferably the lysis buffer may have a pH in the range of from 4 to 11, preferably of from 7 to 10, and most preferably of from 8 to 9.

In addition to a lysis buffer a proteolytic agent may be added to the mixture in step 3. The proteolytic agent may already be comprised in the lysis buffer added to the sample in step 3, as well. Said proteolytic agent may preferably be selected from the group comprising proteases and non-enzymatic proteolytic compounds, preferably may represent proteinase K, trypsin, chymotrypsin, papain, pepsin, pronase, endoproteinase Lys-C, bromocyane, recombinant Bacillus proteases such as for example QIAGEN protease Lysozyme or a mixture thereof.

The step of incubating the mixture obtained after adding the aqueous lysis buffer to the sample according to step 4 may preferably be carried out at a temperature in the range of from 15 to 95° C., preferably of from 20 to 70° C., and most preferably of from 37 to 65° C., including 56° C. This incubation may preferably be carried out for 30 seconds to 24 hours, more preferably for 45 seconds to 12 hours, even more preferably for 50 seconds to 5 hours and most preferably for 1 minute to 2 hours. However, both, temperature and time of incubation may vary with the kind, amount and age of the sample, and the lysis buffer employed. This is well known to a person skilled in the art, and optimum lysis conditions, in particular in respect of incubation time and temperature can be easily determined by a person skilled in the art by means of routine experiments. In many cases, it may also be preferred to carry out a "two-step incubation" procedure, first incubating the mixture at a temperature in the range of 37 to 65° C. for e.g. about 1 min to about 3 h, then optionally separating the organic phase from the aqueous phase and incubating the latter at a temperature of about 90° C. for e.g. about 10 min to about 5 h. Optionally separating of the organic phase from the aqueous phase can be done only when the incubation of 90° C. was already carried out. In the latter case evaporation of the aqueous phase is decreased.

The step of isolating and/or purifying the nucleic acid comprised in the aqueous phase according to step 6 may preferably be carried out by means of at least one chromatographic and/or solid phase-based method, preferably selected from the group comprising normal and reversed-phase chromatography, gel filtration chromatography, ion exchange chromatography, reversed phase chromatography, triple helix affinity chromatography, and chaotrope-free affinity binding (adsorption), including adsorption to silica or polystyrol matrices/surfaces mediated by binding agents. Alternatively or in addition, the nucleic acids may as well be purified by selective precipitating either the nucleic acids, for example using a cationic surfactant such as CTAB, or impurities/undesired further compounds present in the sample, for example using ammonium sulphate to precipitate proteins.

The bi- or multi-phasic lysis procedure according to the present invention is compatible with a wide range of different procedures for isolating and/or purifying nucleic acids known from the state of the art, such as for example the procedures according to the commercially available QIAamp, AllPrep DNA/RNA and QIAsymphony tissue kits (all of them QIAGEN, Hilden, Germany). Depending upon the procedure used for isolating and/or purifying the nucleic acids, the organic phase, comprising the dissolved wax and the wax-solubilizing agent, may be separated from the aqueous phase in optional step 5 before further processing the aqueous phase in order to isolate and/or purify the nucleic acids. If for example adsorption to beads, e.g. a chaotrope or non-chaotrope mediated adsorption to silica beads is employed for isolating and/or purifying the nucleic acids from the aqueous phase, it is in many cases not necessary to separate the organic phase from the aqueous phase in a preceding step, in particular if no chaotrope is present in the mixture. If, on the other hand the mixture comprises e.g. guanidinium chloride, the organic phase may advantageously be separated from the aqueous phase before contacting the latter with the solid phase. In methods employing a gel filtration chromatographic step a removal of the organic phase from the aqueous phase prior to the step of applying the latter on the chromatographic column may be advantageous, even if no chaotrope is present in the aqueous phase. After separating the aqueous from the organic phase, it may be preferred to control and optionally adjust the volume of the aqueous phase to compensate for a possible loss of water/buffer during phase separation prior to chromatography.

For example, it may be preferred to combine the principle of lysis in a bi- or multi-phasic system described in the present invention with the lysis procedure and/or the gel chromatographic procedure described in co-pending applications of application number EP 10 003 759.7, EP 10 003 765.4 and EP 10 003 766.2. The method may additionally be combined with the method for RNA removal according to co-pending application EP 10 003 767.0. In a preferred protocol, the wax-embedded sample may be simultaneously mixed with a wax-solubilizing agent according to the present invention, and an appropriate volume of a lysis buffer according to EP 10 003 759.7, comprising at least an anionic surfactant and optionally a buffering substance and/or a proteinase, but being essentially free of chelating or complexing agents. The paraffin may be dissolved as described above, for example by vortexing the sample in contact with the wax-solubilizing agent and optionally incubating the mixture, e.g. at a temperature of preferably about 50 to 65° C. for 5 to 15 minutes. At this point, the aqueous phase and the organic phase may already be separated from each other if desired, for example by removing the lower aqueous phase, e.g. by carefully pipetting. Lysis of the cell material in the sample and removal of crosslinks resulting from formaldehyde fixation of the sample may be completed by a second incubation step, for example for 10 to 60 minutes, preferably for 15 to 45 minutes and more preferably for 25 to 35 minutes, preferably at temperatures of about 90° C. The lysis buffer may preferably comprise an anionic surfactant ion, which after incubation according to step 4 may essentially be removed from the sample by precipitation using monovalent ions of alkali metals and/or divalent ions of alkaline earth metals, preferably selected from the group comprising $Rb^+$, $Cs^+$, $Ca^{2+}$, $Sr^{2+}$, $Ba^{2+}$, or a mixture thereof, prior to isolating and/or purifying the nucleic acid from the aqueous phase, preferably by gel filtration chromatography. For selectively precipitating the anionic surfactant ions from the aqueous sample solution a precipitating solution as described in EP 10 003 765.4, comprising monovalent ions of alkali metals and/or divalent ions of alkaline earth metals, preferably selected from the group comprising $Rb^+$, $Cs^+$, $Ca^{2+}$, $Sr^{2+}$, $Ba^{2+}$, or a mixture thereof may be added to the sample. To ensure completeness of precipitate formation, the mixture may optionally be incubated, for example at temperatures of about from −5 to 5° C. for about 3 to 20 minutes.

From this mixture the DNA may preferably be isolated (and simultaneously purified) using the gel chromatographic device and the method described in EP 10 003 766.2, i.e. a chromatographic device comprising a gel-forming polymer matrix having a size exclusion limit of around 150 to 500 bp, wherein the chromatographic device preferably may be in the form of a so-called spin column and elution preferably may be carried out by "spinning" the column, i.e. moving the eluting solvent through the column by centrifugation. Using this combination of methods and devices, highly purified DNA, in particular gDNA of a very low salt and further inhibitor content is obtained, which can be directly used in downstream applications including techniques such as PCR, ligation, hybridization etc., without the need for further processing steps, such as for example a buffer exchange.

Reference made to the above mentioned co-pending applications should be understood as an exemplary application of the method of the present invention. However, the method of the present invention is not limited to being combined with the particular protocols and devices mentioned above, but performs equally well in combination with for example ion exchange chromatography, reversed phase chromatography and chaotrope-free affinity binding, giving high yields of nucleic acids with excellent purity and of low salt and further inhibitor content, which can be directly used in the downstream applications mentioned above.

The nucleic acids to be isolated and/or purified according to the present invention preferably may be selected from the group comprising ribonucleic acids (RNA) and desoxyribonucleic acids (DNA), including naturally occurring, recombinant and/or chemically or biotechnically engineered nucleic acids of eukaryotic, prokaryotic or viral origin, including gDNA, cDNA, rRNA, miRNA, sRNA, piRNA, snRNA, LNA (locked nucleic acids), PNA (peptide nucleic acids), or fragments thereof, without being limited to these.

When employing a suitable lysis buffer, such as, for instance, buffer PKD, commercially available from QIAGEN (Hilden, Germany), even different kinds of nucleic acids may be isolated from the same sample using the method of the present invention (as shown in example 7). Preferably the nucleic acids may represent DNA, more preferably DNA having a length of at least 100 bp.

The invention further provides the use of a solvent selected from the group comprising linear, branched and cyclic $C_{10}$-$C_{16}$ alkanes, more preferably selected from the group comprising $C_{13}$-$C_{16}$ alkanes, and most preferably represents tetradecane, pentadecane, or hexadecane, for the removal of wax from a wax-embedded sample in a method for extracting, isolating and/or purifying nucleic acids from a cross-linked wax-embedded sample, preferably a FFPE-sample, preferably in the method described above, wherein the step of lysing the crosslinks in the sample preferably may be carried out in a bi- or multi-phasic mixture formed of at least one or more of said solvent(s) and an aqueous lysis buffer.

The method of the present invention further provides a kit for extracting, isolating and/or purifying nucleic acids from a wax-embedded sample as described above, comprising (1) a wax-solubilizing agent, preferably a wax-solubilizing agent as described above, and optionally (2) instructions for carrying out the lysis in a bi- or multi-phasic system according to step 3. The kit further may comprise one or more additional components selected from the group comprising (3) an aqueous lysis buffer, preferably a lysis buffer as described above (4) a proteolytic agent, preferably a proteolytic agent as described above, and (5) a solid phase for chromatography and/or affinity binding.

EXAMPLES

Example 1

Effect of Dewaxing FFPE Samples Using Xylene in a Method for Isolating Nucleic Acids Including SDS Precipitation ("Single Step Isolation")

In preliminary experiments sections from FFPE tissue blocks (each 10 µm thick) were lysed in 80 µL of a lysis buffer described in EP 10 003 759.7, comprising 25 mmol/L TRIS and 25 mmol/L SDS at pH 8.5, supplemented with 10 µL QIAGEN protease (QIAGEN, Hilden, Germany, 2.5 AV/ml) and 1 µL RNase A (10 U/ml) (QIAGEN, Hilden, Germany). The mixture was vortexed and then incubated at 56° C. for 1 h, followed by a second incubation step at 90° C. for 1 h. 10 µL of a precipitating solution were then added for precipitating dodecylsulfate ions from the sample as described in EP 10 003 765.4, said solution comprising 1.0 mol/L $SrCl_2$. The mixture was vortexed and incubated on ice for 10 min. The gDNA present in the sample was then isolated by transferring the whole lysate to a gel filtration column as described in EP 10 003 766.2, comprising Sephacryl resin S-400 HR with a size exclusion limit of 271 bp, and eluting the nucleic acids by centrifugation at 700×g for 3 min.

gDNA of high purity and low sodium dodecylsulfate content was obtained, however, the yield obtained in different runs varied. It was assumed that dissolution of paraffin may be not effectual enough.

Accordingly, in a first approach xylene was tested as a solvent for removing paraffin from the FFPE tissue samples in a separate step prior to applying a lysis procedure followed by a gel filtration chromatography as described above. Thus, in each experiment three sections from rat liver FFPE samples (each 10 µm thick) either were treated first using xylene as a dewaxing agent or were directly subjected to a lysis procedure described above, the first incubation step either being carried out at 56° C. or at 62° C., respectively.

Dewaxing was carried out by applying 1 mL of xylene to the respective samples, vortexing the mixture for 10 s, centrifuging at 14,000 rpm for 2 min and then separating the supernatant by pipetting. 1 mL of EtOH was added to the aqueous phase, the mixture was vortexed and centrifuged at 14,000 rpm for 2 min. The supernatant was then separated by pipetting. The open tube containing the aqueous phase was left to stand at room temperature for about 20 min to allow residual EtOH to evaporate. Lysis and isolation of DNA was then carried out as described above. The residual amount of SDS in the eluates obtained after gel filtration chromatography was determined as described in EP 10 003 765.4.

Figure 1:
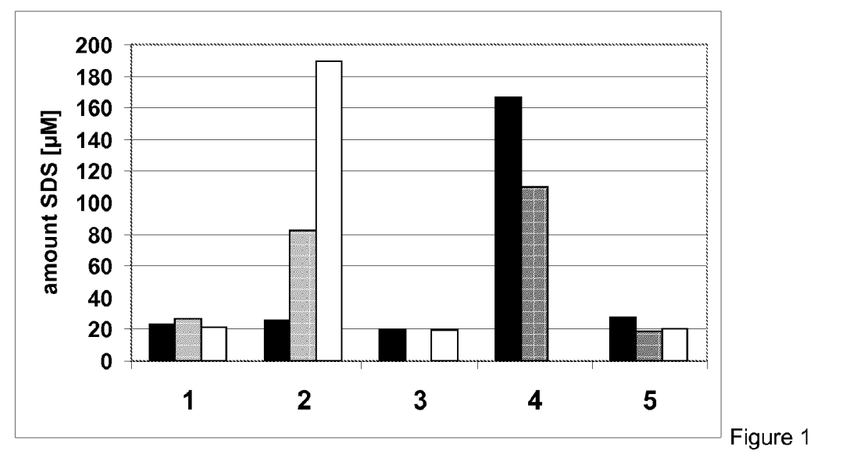
FIG. 1 shows the effect of the presence (columns 2 and 4, respectively) or absence (columns 3 and 5, respectively) of a xylene dewaxing step on a particular lysis and isolation protocol (example 1). For comparison in column 1 the results obtained using the commercially available QIAamp kit according to the manufacturer's protocol are shown as well.

The results are presented in FIG. 1 (column 2: xylene dewaxing step and first incubation step at 62° C.; column 3: without xylene dewaxing step and first incubation step at 62° C.; column 4: xylene dewaxing step and first incubation step at 56° C.; column 5: without xylene dewaxing step and first incubation step at 56° C.). For comparison, three sections from the same FFPE block (each 10 µm) were processed using a QIAamp kit (QIAGEN, Hilden, Germany) according to the manufacturer's instructions, including a first one hour incubation step at 56° C., followed by a second one hour incubation step at 90° C. (column 1 in FIG. 1).

From FIG. 1 it can be seen that using xylene as a dewaxing agent has an undesired effect on the amount of residual sodium dodecylsulfate (SDS) in the eluate obtained after gel filtration chromatography in the so-called "single step" purification procedure described in EP 10 003 759.7, EP 10 003 765.4 and EP 10 003 766.2, respectively.

Example 2

Figure 2:
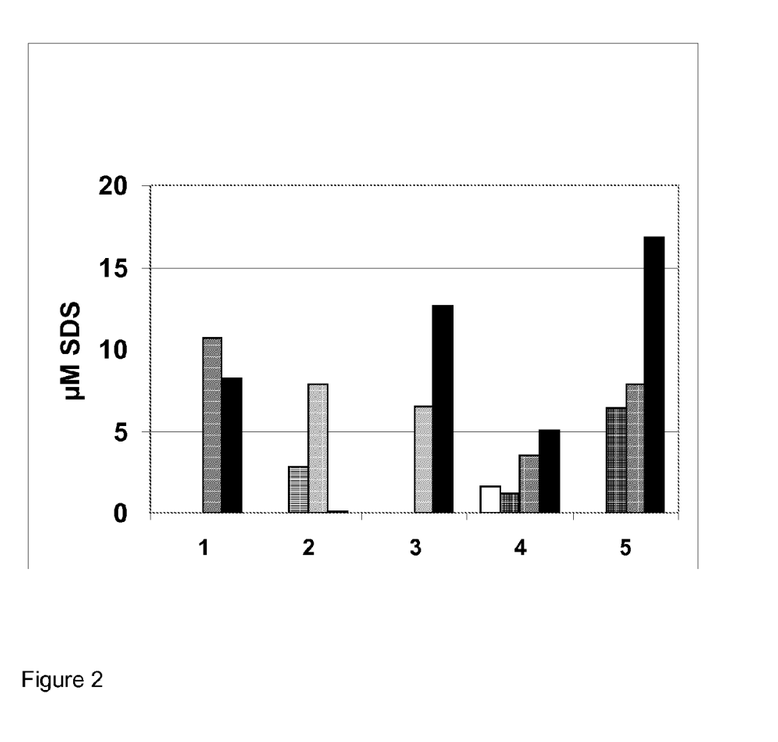
FIG. 2 shows the amount of residual SDS present in the eluate obtained by gel filtration chromatography when using the biphasic lysis procedure according to the present invention employing different solvents (example 2).

Effect of Dewaxing of FFPE Samples Using Different Alkanes in a Method for Isolating Nucleic Acids Including SDS Precipitation Next, linear alkanes of different chain length, i.e. tridecane (denoted "1" in FIG. 1), tetradecane ("2" in FIG. 2), pentadecane ("3" in FIG. 2), and hexadecane ("4" in FIG. 2) instead of xylene were used as dewaxing agent. All of these solvents were able to completely dissolve the solid paraffin in paraffin-embedded samples within only a few minutes (about 1 to 2 min) at room temperature. After dewaxing and removing the organic liquid phase, the samples were processed according to the "single step isolation process" as described in example 1. A further sample was processed without any dewaxing step ("5" in FIG. 2).

The amount of SDS present in the eluates obtained by first dewaxing FFPE tissue sections with the respective alkane and then isolating the gDNA present in the samples according to the so-called single step protocol described above are presented in FIG. 2. The amount of SDS was determined as described above.

Each experiment was carried out four times. In several samples the amount of SDS was even too low to be detected using the procedure applied for determination.

Example 3

Simultaneous Dewaxing and Lysing in a Biphasic System

Four sections each from a FFPE block (10 µm each) were mixed with 100 µL of the lysis buffer described in example 1, 10 µL Proteinase K (QIAGEN, Hilden, Germany) and 100 µL of n-decane, n-dodecane, n-hexadecane, kerosene, and octylether respectively, and vortexed until the whole section was dissolved, which took less than 1 min at room temperature in each case. The mixture was then incubated at 56° C. for 5 min. The mixture was centrifuged at about 20000×g for 5 min to separate the aqueous from the organic phase. The aqueous phase was removed and incubated at 90° C. for 1 h. Then 10 µL of a SrCl$_2$ solution described in example 1 were added, the mixture was vortexed and incubated for 10 min in an ice bath. The mixture was then centrifuged at full speed for 5 min, and the nucleic acids of 100 µL of the supernatant were purified using the single step protocol described in example 1.

Figure 3:
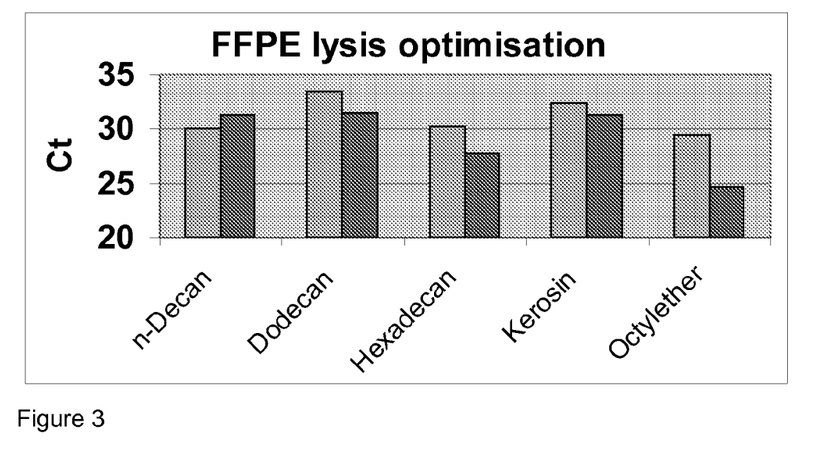
FIGS. 3 and 4 show the influence of the dewaxing solvent on the Ct values obtained in a subsequent PCR (example 3).

The gDNA obtained was amplified in a PCR. 2 µl of the eluate were amplified in a 25 µl PCR sample using a primer pair annealing to the 18S rDNA, resulting in a 149 bp fragment. A double concentrated SyBr-Green Mastermix (12.5 µL), 1.25 µL of each a forward and a reverse 18 S primer (c=10 µM) and 2 µL eluate and 8 µl water as a template were used. The reaction was carried out on a RotorGene 3000 (Corbett Research, Sydney). Denaturating was carried out for 15 s at 94° C., annealing for 30 s at 56° C. and extending at 72° C. for 30 s. In total, 40 cycles were carried out. The Ct values obtained are shown in FIG. 3. It can be seen that gDNA which can be readily amplified in a subsequent PCR can be obtained using a biphasic lysis procedure described above, employing each of n-decane, n-dodecane, n-hexadecane, kerosene, or octylether, respectively. n-Hexadecane and octylether gave the lowest Ct values in the subsequent PCR; using octylether, however, the residual amount of SDS in the eluate was higher than when using hexadecane.

Figure 4:
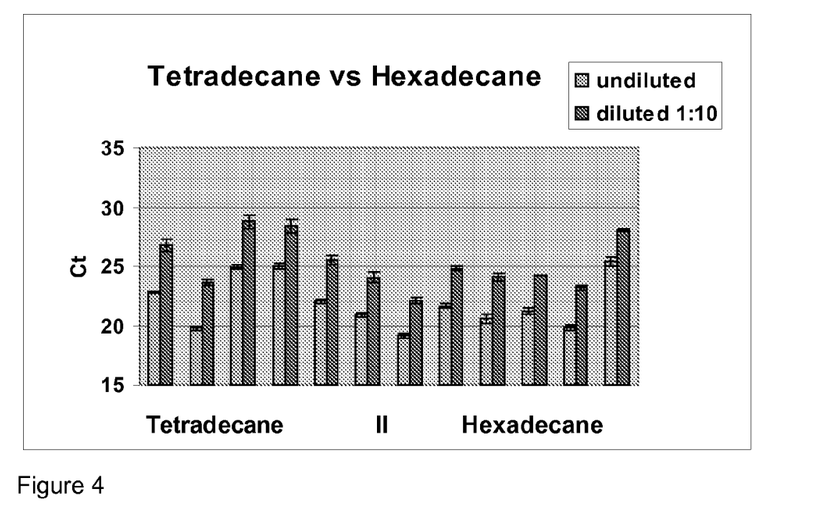

In further experiments, tetradecane and hexadecane were compared, using the procedure described above and carrying out six runs for each solvent, respectively. The eluate obtained after gel filtration chromatography, comprising the purified gDNA, was used in PCR, either as obtained (denoted "undiluted" in FIG. 4) or after being diluted by a factor of 10 using water, respectively. The results are presented in FIG. 4.

Example 4

Investigation on the Range of Fragment Length which can be Amplified from FFPE Samples Lysed in a Biphasic Mixture It is well known to a person skilled in the art that the maximum fragment length of nucleic acids which can be isolated and/or amplified from FFPE samples is limited due to the effects of cross-linking and their removal in said samples. To test whether or not the biphasic lysis procedure according to the present invention further limits the fragment length which can be processed in a PCR with four different target lengths was carried out using eluates obtained after dewaxing and lysing FFPE samples employing n-hexadecane as a dewaxing agent and purifying the mixture obtained by the single step protocol. As it is shown in table 1, fragments of 78 bp, 463 bp, 725 bp and 815 bp, respectively, could be readily amplified in a PCR reaction. Some additional shorter fragments only were observed in the electrophoresis gel obtained from PCR reaction of the 815 bp fragment (data not shown).

TABLE 1

| Fragment Length [bp] | ct |
|---|---|
| 78 | 24.40 |
| 463 | 28.90 |
| 725 | 34.10 |
| 815 | 40.99 |

Example 5

Isolation and Purification of gDNA from FFPE Rat Liver Samples

Two sections from a FFPE rat liver block, each 10 µm thick, were mixed with 150 µL of the lysis buffer described in example 1, 10 µL of Proteinase K (QIAGEN, Hilden, Germany), 1 µL of RNase (QIAGEN, Hilden, Germany), and 150 mL n-hexadecane. The samples were vortexed and then incubated at 56° C. for about 10 min. The samples were then centrifuged at full speed in order to separate the phases and 130 µL of the lower aqueous phase containing the DNA were removed by pipetting and transferred into a new tube. After incubating the aqueous samples for 30 min at 90° C., the samples may be centrifuged for a short time in order to remove drops from inside the lid, before adding 10 µL of the SrCl$_2$ solution described in example 1. The mixture was vortexed and then incubated in an ice bath for 10 min. The whole mixture was then transferred onto a pre-centrifuged (700×g, 3 min) single step column as described in example 1. The gDNA was purified by centrifuging the column at 700×g for 3 min. The eluate containing the purified gDNA was then analysed as described below. The DNA obtained can directly be used in downstream applications without any further purification steps.

10 µL of the eluates were amplified in a 18S RT-PCR as described in Example 3, giving a Ct value of 15.12 if the eluate was used in the PCR without diluting it previously.

The residual amount of SDS present in the eluates was as low as between about 1 to 3 µM.

Example 6

Dewaxing Using Hexadecane Instead of Xylene in a QIAamp Protocol

Two sections of a FFPE rat liver block (each 10 µm) were processed either using the FFPE QIAamp kit according to the manufacturer's instructions (using xylene for dewaxing) (alternative a)) using n-hexadecane for dewaxing and removing the dewaxing agent prior to lysis (alternative b)), or according to the present invention, employing n-hexadecane for dewaxing while simultaneously lysing the sample (alternative c)).

Figure 5:
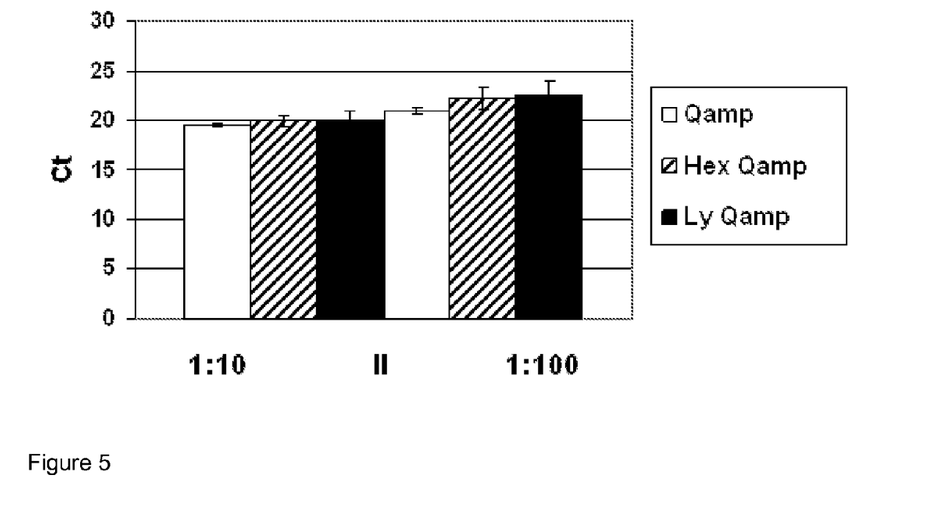
FIG. 5 shows the effect of replacing the original dewaxing solvent xylene (denoted "Qamp" in FIG. 5) by hexadecane in the QIAamp protocol (denoted "Hex Qamp" in FIG. 5) as well as the effect of replacing the separate dewaxing and lysis steps according to the QIAamp protocol by the biphasic protocol according to the present invention ("SiStLy Qamp") on the Ct value obtained in a PCR using the obtained eluates at a dilution ratio of 1:10 or 1:100, respectively (example 6).

Alternative a) (Denoted "Qamp" in FIG. 5)

According to the QIAamp standard protocol a 10 µm section from a FFPE block was suspended in 1 mL of xylene, mixed by vortexing for 10 s and then centrifuged at full speed for 2 min. After removing the upper layer by pipetting, residual xylene was extracted by adding 1 µL of ethanol, mixing, centrifuging and removing the upper phase by pipetting. The open tubes were then incubated at room temperature for about 20 min until residual ethanol has been evaporated. To lyse the pellet, it was suspended in 180 µL of buffer ATL (QIAGEN, Hilden, Germany), 20 µL Proteinase K (QIAGEN, Hilden, Germany, 2.5 AU/ml) were added and the samples are mixed by vortexing. The samples were then incubated at 56° C. for 1 h in a first incubation step, followed by a second incubation step at 90° C. for 1 h. After cooling to room temperature 1 µL of RNase A (QIAGEN, Hilden, Germany) was added to the sample for RNA digestion. 200 µL of buffer AL were added and the mixture was vortexed. 200 µL of ethanol are then added, the mixture was vortexed again and then transferred to a QIAamp MinElute column. Said column was centrifuged at 6000×g for 1 min. The flow-through was discarded and the column was washed with 500 µL of a first washing buffer AW 1 (QIAGEN, Hilden, Germany), followed by 500 µL of buffer AW 2 (QIAGEN, Hilden, Germany), in both cases moving the washing buffer down the column by centrifuging at 6000×g for 1 min. The column was then centrifuged at full speed for about 3 min to remove residual traces of buffer, before finally eluting the purified gDNA by applying 100 µL of RNase-free water to the membrane inside the column, incubating it for about 1 min at room temperature and finally centrifuging the column at full speed for 1 min.

Alternative b) (Denoted "Hex Qamp" in FIG. 5)

To the section 180 µL of buffer ATL, 20 µL of Proteinase K and 100 µL of hexadecane were added, the mixture was vortexed and then incubated at 56° C. for 10 min. The mixture was centrifuged for 2 min at full speed and the lower aqueous phase was separated and transferred to a new tube. Further processing of the sample was carried out according to the above mentioned QIAamp protocol, starting with the incubation step at 90° C. for 1 h.

Alternative c) (Denoted "Ly Qamp" in FIG. 5)

In the protocol modified according to the present invention, the sections were not treated with xylene first, but 150 µL of the lysis buffer described in example 1, 10 µL Proteinase K, 1 µL RNAse A and 150 µL hexadecane were added to the sections. The mixture was vortexed and incubated for 10 min at 56° C. After centrifugation, 120 µL of the lower aqueous phase were transferred into a new tube and incubated for 30 min at 90° C. 200 µL of buffer AL (QIAGEN, Hilden, Germany) and 200 µL ethanol were added to the sample and the nucleic acids then purified according to the QIAamp protocol using a QIAamp MinElute column and eluting with 100 µL of water.

The gDNA obtained was then amplified in a 18 S-PCR using a double concentrated SyBr-Green Mastermix (12.5 µL), 1.25 µL of each a forward and a reverse 18 S primer (c=10 µM) and 10 µL of the eluate as a template, diluted at a ratio of either 1:10 or 1:100, respectively using water. The reaction was carried out on a RotorGene 3000 (Corbett Research, Sydney). Denaturating was carried out for 15 s at 94° C., annealing for 30 s at 56° C. and extending at 72° C. for 30 s. In total, 40 cycles were carried out.

The results are presented in FIG. 5. It can be seen, that using hexadecane for dewaxing, the Ct values obtained are almost as good as when using toxic xylene for dewaxing. In addition, it can be seen that not only lysis and dewaxing, but also RNA digestion may be carried out in the multiphasic system.

Example 7

Isolation of Both, RNA and DNA, from the Same FFPE Sample

In this experiment 18 sections from rat kidney FFPE tissue (10 µm per section, two sections per run) were processed according to the method described in copending European application 10 001 995.9 using either different solvents for dewaxing prior to the lysis step or the multiphasic lysis procedure according to the present invention. For comparison of two further samples RNA was isolated using the RNeasy FFPE Kit (QIAGEN; Hilden, Germany) according to the manufacturer's instructions (samples 19 and 20).

A. Dewaxinq and Lysis

A1 Using Xylene in a Separate Dewaxing Step Prior to Lysis (Samples 1 and 2)

1 mL of xylene was added to the sections. The mixtures were vortexed for 10 s and then centrifuged at 14,000 rpm for 2 min. The supernatant was carefully removed and 1 mL of ethanol was added to the remaining pellet. The mixtures were vortexed and then centrifuged at 14,000 rpm for 2 min. The supernatant was carefully removed and the vials were incubated for 10 min at 37° C. to evaporate remaining ethanol.

A2 Using Heptane/Methanol in a Separate Dewaxing Step Prior to Lysis (Samples 3 to 8)

1 mL heptane was added to the sections. The mixtures were vortexed for 10 s and then either incubated for 1 h (samples 3 and 4) or 15 min (samples 5 and 6) at room temperature, respectively, or simply shaken for a few seconds at room temperature (samples 7 and 8). 50 µL of methanol were then added, the mixtures were vortexted for 10 s and then centrifuged at 9,000×g for 2 min. The supernatant was carefully removed and the pellet was left to dry at room temperature for 5 min.

A3 Using Hexadecane in a Separate Dewaxing Step Prior to Lysis (Samples 9 to 12)

1 ml of hexadecane was added to each of the sections. The mixtures were vortexed for 10 s and then either left to stand at room temperature for 1 h (samples 9, 10) or further mixed by shaking (samples 11, 12) for a few seconds. The mixture was then centrifuged at room temperature, either at full speed (about 20000×g) or at 9,000×g (samples 11, 12). After carefully removing the supernatant the vials were incubated for 10 min at 37° C. to evaporate remaining organic solvent.

To each of the pellets obtained from the above dewaxing procedures A1 to A3 150 µL of buffer PKD (QIAGEN, Hilden, Germany) and 10 µL of proteinase K (QIAGEN, Hilden, Germany) were added. The mixtures were vortexted and then incubated at 56° C. at 1,400 rpm in a shaking incubator for 15 min. The samples were then incubated on ice for 3 min and afterwards centrifuged at 20,000×g for 30 min to obtain a supernatant, mainly comprising RNA, and a pellet, mainly comprising DNA.

A4 Dewaxing with Simultaneous Lysis According to the Present Invention (Samples 13 to 18)

150 µL of buffer PKD was added to the sections, followed by 10 µL of proteinase K and 200 µL of n-hexadecane. The mixtures were manually shaken and then incubated for 15 min at 56° C. on a shaking incubator at 1,400 rpm. The samples were then centrifuged at 20,000×g for 30 min. After centrifugation, four "phases" were obtained (counted from top to bottom): 1. a clear and colourless liquid, 2. a whitish cloudy liquid, 3. a clear and slightly greasy liquid, and 4. a pellet.

In samples 13 to 15 phases 1 and 2 were separated and discarded. Phase 3 was separated from the pellet (phase 4) and transferred into a new tube for processing further.

In each of samples 16 to 18 all liquid phases (1 to 3) together were removed from the pellet and centrifuged at full speed for 1 min. Again three liquid phases were obtained. Said three liquid phases were separated from each other. The upper liquid phase (hereafter denoted "oP") was transferred into a new tube, the middle whitish phase was discarded and the lower aqueous phase (hereafter denoted "uP") was transferred to a new tube.

B. Isolation of RNA from the Liquid Phases Using on-Column DNase Digest

The liquid phases obtained from samples 1 to 18 were incubated for 15 min at 80° C. at 450 rpm in a thermoshaker and were then allowed to cool to room temperature for 5 min. 320 µL of buffer RLT (QIAGEN, Hilden, Germany) were added and the samples were mixed. 1.12 mL of ethanol were then added, the samples were mixed thoroughly and applied onto a RNeasy MinElute spin column (QIAGEN, Hilden, Germany) in aliquots having a maximum volume of 700 µL. After the application of each aliquot the columns were centrifuged at 10,000 rpm for 1 min and the flowthrough was discarded. For on-column DNase digest the columns were first washed with 500 µL of a buffer comprising 1.5 M GTC and 75% ethanol by centrifuging the columns at 10,000 rpm for 1 min. The flowthrough was discarded, 70 µL of buffer RDD (QIAGEN, Hilden, Germany) and 10 µL of DNase I solution (2.7 KU/µl) were mixed and added to the columns, which then were incubated for 15 min at room temperature. 500 µL of the above mentioned buffer comprising GTC and ethanol were added onto the columns, the columns were centrifuged at 10,000 rpm for 1 min. Each flowthrough was collected and applied again to the same column for rebinding. The columns were centrifuged at 10,000 rpm for 1 min and now the flowthrough was discarded. 700 µL of buffer RPE (QIAGEN, Hilden, Germany) were added onto the columns and the columns were centrifuged at 10,000 rpm for 1 min. The flowthrough was discarded and the RPE treatment was repeated. The columns were then centrifuged at 14,000 rpm for 5 min with open lid. 30 µL of water were pipetted directly on the column membrane, incubated at room temperature for 1 min and then centrifuged for 1 min at 14,000 rpm to obtain approximately 30 µL of an eluate which was collected and stored at −20° C. until being processed further.

C. Isolation of DNA from the Pellets without RNase Digest

180 µL of buffer ATL (QIAGEN, Hilden, Germany) were added to each of the pellets, followed by 20 µL of proteinase K. The samples were incubated at 56° C. for 1 h in a shaking incubator at 1,400 rpm, followed by a second incubation step at 90° C. for 2 h. 200 µL of buffer AL (QIAGEN, Hilden, Germany) were added, and the samples were immediately mixed thoroughly, 200 µL of ethanol were then added and the samples were again immediately mixed thoroughly. The mixtures were pipetted each onto a QIAamp MinElute column (QIAGEN, Hilden, Germany). Said columns were centrifuged at 10,000 rpm for 1 min and the flowthrough was discarded. The columns were washed using 700 µL of buffer AW1 and centrifuging the column for 1 min at 10,000 rpm. The flowthrough was discarded and the columns were washed using 700 µL of buffer AW2 and centrifuging at 10,000 rpm for 1 min, again discarding the flowthrough. 700 µL of ethanol were then added onto each of the columns and the columns were centrifuged at 10,000 rpm for 1 min. The flowthrough was discarded and the columns were centrifuged for 5 min at 14,000 rpm with open lid to dry the membranes. 30 µL of buffer ATE (QIAGEN, Hilden, Germany) were pipetted directly onto the column membrane each, the columns were incubated 1 hour and then centrifuged 1 hour at 10,000 rpm, collecting the flowthrough to obtain approximately 30 µL eluate of each column. The eluates were stored at −20° C. until being processed further.

In table 1, a short overview on how the different samples were processed is given.

TABLE 1

| Nr. | sample 2 × 10 µm | dewaxing solvent | time | centrifugation | further processing |
|---|---|---|---|---|---|
| 1 | kidney | xylene/EtOH | 10 s vortexing | 2 min full speed | according to |
| 2 | (rat) | (1 mL) | | | EP application No. 10 001 995.9 |
| 3 | | 1 mL heptane/ | 10 s vortexing | 3 min 9000 xg | |
| 4 | | 50 µL MeOH | 1 h incubating at RT | | |
| 5 | | 1 mL heptane/ | 10 s vortexing | 3 min 9000 xg | |
| 6 | | 50 µL MeOH | 15 min incubating at RT | | |
| 7 | | 1 mL heptane/ | 10 s vortexing | 3'9000 xg @RT | |
| 8 | | 50 µL MeOH | shaking | | |
| 9 | | hexadecane | 10 s vortexing | 2 min full speed | |
| 10 | | (1 mL) | 1 h incubating at RT | | |
| 11 | | hexadecane | 10 s vortexing | 3 min 9000 xg | |
| 12 | | (1 mL) | shaking | | |
| 13 | | dewaxing and simultaneous lysis: | | | discard the two upper phases |
| 14 | | PKD + proteinase K + hexadecane | | | lower liquid phase used for RNA isolation |
| 15 | | 15 min incubating at 56° C., 30 min | | | pellet used for DNA isolation |

TABLE 1-continued

| Nr. | sample 2 × 10 μm | dewaxing solvent | time | centrifugation | further processing |
|---|---|---|---|---|---|
| 16 oP | | | | centrifugation at full speed to obtain | pellet used for DNA isolation |
| 17 oP | | | | | centrifugation of all three liquid phases |
| 18 oP | | | | | 1 min at full speed |
| 16 uP | | | | | collect upper (oP) and lower phase (uP) |
| 17 uP | | | | | for RNA isolation |
| 18 uP | | | | | discard middle phase |
| 19 | | | | miRNyFFPE | |
| 20 | | | | | |

The amount of RNA (denoted with an additional "a") and DNA (denoted with an additional "b"), respectively, was optically determined at a Nanodrop (Thermo Scientific, Wilmington, USA). The results are presented in table 2.

TABLE 2

| Nr. | c [ng/μL] | A260 | A280 | 260/280 | 260/230 |
|---|---|---|---|---|---|
| A = RNA | | | | | |
| 1a | 200.7 | 5.018 | 2.497 | 2.01 | 1.58 |
| 2a | 222 | 5.550 | 2.811 | 1.97 | 1.33 |
| 3a | 215.9 | 5.397 | 2.708 | 1.99 | 1.52 |
| 4a | 210.1 | 5.252 | 2.640 | 1.99 | 1.46 |
| 5a | 214.1 | 5.352 | 2.701 | 1.98 | 1.11 |
| 6a | 198.8 | 4.969 | 2.480 | 2.00 | 1.36 |
| 7a | 189.2 | 4.729 | 2.332 | 2.03 | 1.39 |
| 8a | 203.4 | 5.086 | 2.545 | 2.00 | 1.62 |
| 9a | 160.2 | 4.005 | 1.960 | 2.04 | 1.66 |
| 10a | 162.7 | 4.068 | 2.031 | 2.00 | 1.52 |
| 11a | 187.8 | 4.696 | 2.362 | 1.99 | 1.3 |
| 12a | 199.4 | 4.986 | 2.462 | 2.02 | 1.64 |
| 13a | 138.4 | 3.461 | 1.753 | 1.97 | 1.47 |
| 14a | 119.8 | 2.994 | 1.521 | 1.97 | 1.47 |
| 15a | 137.3 | 3.432 | 1.724 | 1.99 | 1.62 |
| 16a oP | 6.563 | 0.164 | 0.111 | 1.47 | 0.06 |
| 17a oP | 5.145 | 0.129 | 0.086 | 1.49 | 0.06 |
| 18a oP | 8.3 | 0.207 | 0.132 | 1.57 | 0.22 |
| 16a uP | 120.4 | 3.009 | 1.513 | 1.99 | 1.58 |
| 17a uP | 140.8 | 3.520 | 1.775 | 1.98 | 1.18 |
| 18a uP | 142.1 | 3.553 | 1.827 | 1.94 | 1.2 |
| 19 | 187 | 4.675 | 2.309 | 2.03 | 1.85 |
| 20 | 187.5 | 4.688 | 2.286 | 2.05 | 1.92 |
| B = DNA | | | | | |
| 1b | 66.64 | 1.333 | 0.760 | 1.75 | 3.84 |
| 2b | 94.07 | 1.881 | 1.054 | 1.78 | 1.77 |
| 3b | 78.95 | 1.579 | 0.911 | 1.73 | 1.81 |
| 4b | 81.27 | 1.625 | 0.896 | 1.81 | 0.4 |
| 5b | 100.6 | 2.012 | 1.066 | 1.89 | 0.96 |
| 6b | 35.6 | 0.712 | 0.391 | 1.82 | 1.66 |
| 7b | 116.3 | 2.325 | 1.244 | 1.87 | 1.5 |
| 8b | 100.7 | 2.015 | 1.090 | 1.85 | 1.94 |
| 9b | 96.33 | 1.927 | 1.048 | 1.84 | 1.74 |
| 10b | 83.08 | 1.662 | 0.909 | 1.83 | 1.67 |
| 11b | 93.11 | 1.862 | 1.021 | 1.82 | 1.84 |
| 12b | 95.53 | 1.911 | 1.039 | 1.84 | 0.87 |
| 13b | 103.2 | 2.065 | 1.079 | 1.91 | 1.58 |
| 14b | 94.82 | 1.896 | 1.020 | 1.86 | 1.43 |
| 15b | 93.14 | 1.863 | 1.017 | 1.83 | 1.95 |
| 16b | 87.74 | 1.755 | 0.938 | 1.87 | 1.63 |
| 17b | 121 | 2.420 | 1.377 | 1.76 | 0.23 |
| 18b | 96.8 | 1.936 | 1.045 | 1.85 | 1.94 |

From these results it can be seen that for both, RNA and DNA, the amount of nucleic acid obtained from a sample which has been lysed in a biphasic mixture according to the present invention are comparable to those obtained using well established standard methods. Regarding the isolation of RNA, the yields as optically determined at a Nanodrop using the method of the present invention are somewhat lower compared to the other methods. In the following RT-PCR experiments, however, a lower amount of RNA in the samples cannot be confirmed by comparing the Ct values obtained. Regarding the isolation of DNA, the method of the present invention gave the highest yield as optically determined by using a Nanodrop.

The RNA obtained was further analyzed on an Agilent 2100 Bioanalyzer (Agilent Technologies, Boblingen, Deutschland) in a so-called nano assay according to the manufacturer's protocol. In table 3 the RNA integrity numbers obtained are presented.

TABLE 3

| Nr. | RIN |
|---|---|
| 1 | 1.8 |
| 2 | 2.4 |
| 3 | 2.4 |
| 4 | 2.6 |
| 5 | 2.6 |
| 6 | 2.9 |
| 7 | 2.6 |
| 8 | 2.2 |
| 9 | 2.4 |
| 10 | 2.2 |
| 11 | 2.4 |
| 12 | 2.3 |
| 13 | 2 |
| 14 | 2.6 |
| 15 | 2.3 |
| 16a oP | — |
| 17a oP | — |
| 18a oP | — |
| 16a uP | 2.4 |
| 17a uP | 2.5 |
| 18a uP | 2.5 |
| 19 | 2.4 |
| 20 | 2.4 |

These results show that not only the amount, but also the quality of the RNA obtained is at least comparable to those obtained using methods well established in the state of the art.

To further evaluate the amount and quality of RNA isolated using the different procedures, a Quantitect SyBr-Green RT-PCR (QIAGEN, Hilden, Germany) using cjun and Madh7, respectively, as a target was carried out according to the manufacturer's standard protocol.

The Ct values obtained in these experiments are presented in table 4.

TABLE 4

| Dewaxing agent and procedure (see above) | Ct Madh7 | Ct cjun | deltaCt cjun −/+ RT |
|---|---|---|---|
| xylene | 23.83 | 29.28 | 10.63 |
| heptane 1 h incubating | 24.10 | 29.45 | 10.55 |

TABLE 4-continued

| Dewaxing agent and procedure (see above) | Ct Madh7 | Ct cjun | deltaCt cjun −/+ RT |
|---|---|---|---|
| heptane 15 min | 24.16 | 29.29 | 10.71 |
| heptane shaking | 24.03 | 29.23 | 10.77 |
| hexadecane 1 h incubating | 24.41 | 29.54 | 9.24 |
| hexadecane shaking | 24.15 | 29.34 | 9.84 |
| hexadecane and simultaneous lysis | 24.69 | 29.66 | 9.67 |
| hexadecane and simultaneous lysis oP | 40.00 | 39.68 | 0.32 |
| hexadecane and simultaneous lysis uP | 24.33 | 29.77 | 9.84 |
| miRNeasy | 23.60 | 29.75 | 3.62 |

Again the results obtained using the biphasic dewaxing/lysis procedure according to the present invention are comparable to those obtained using established standard procedures.

The same holds true for cDNA synthesis using a micro RNA reverse transcription kit (Applied Biosystems/Invitrogen Life Technologies, Carlsbad, US) according to the manufacturer's standard protocol using aliquots of the eluates which had been diluted to a concentration of 20 μg of RNA per 5 μL of sample volume.

The results obtained for miR 16 and miR 30b are again comparable to those obtained using standard methods (miR=microRNA).

TABLE 5

| Dewaxing agent and procedure (see above) | Ct miR16 | Ct miR30b |
|---|---|---|
| xylene | 25.18 | 24.53 |
| heptane 1 h incubating | 24.79 | 24.41 |
| heptane 15 min | 24.81 | 24.38 |
| heptane shaking | 25.06 | 24.49 |
| hexadecane 1 h incubating | 24.88 | 24.32 |
| hexadecane shaking | 24.74 | 24.42 |
| hexadecane and simultaneous lysis | 25.04 | 24.33 |
| hexadecane and simultaneous lysis oP | 35.81 | 37.28 |
| hexadecane and simultaneous lysis uP | 24.55 | 24.19 |
| miRNeasy | 24.42 | 24.11 |

In a further experiment, the amount and the quality of the DNA isolated using the different procedures described above was evaluated in a Quantitect SyBr-Green (QIAGEN, Hilden, Germany) PCR reaction amplifying prnp 78 bp according to manufacturer's standard protocol. The results are presented in table 6.

TABLE 6

| Dewaxing agent and procedure (see above) | Ct prnp78 bp |
|---|---|
| xylene | 24.51 |
| heptane 1 h incubating | 24.50 |
| heptane 15 min | 25.04 |
| heptane shaking | 23.95 |
| hexadecane 1 h incubating | 24.18 |
| hexadecane shaking | 24.20 |
| hexadecane and simultaneous lysis | 23.93 |
| hexadecane and simultaneous lysis oP | 23.85 |

Again, the results obtained using the method of the present invention are comparable or even better than those obtained using methods established in the state of the art.

The invention claimed is:

1. A method for extracting nucleic acids from a wax embedded sample, comprising:
   (a) contacting the sample with a wax-solubilizing agent comprising at least one organic solvent immiscible with water, wherein the at least one organic solvent comprises tetradecane, pentadecane, or hexadecane to form a mixture,
   (b) optionally incubating the mixture obtained in step (a),
   (c) adding an aqueous lysis buffer to the mixture still comprising the wax-solubilizing agent, and
   (d) incubating the mixture obtained in step (c) to obtain a bi- or multi-phasic mixture, comprising (i) at least an organic phase, said organic phase consisting essentially of the dissolved wax and the wax-solubilizing agent, and (ii) an aqueous phase, said aqueous phase comprising the nucleic acids, thereby extracting nucleic acids from the sample,
   wherein steps (a) and (b) are optionally carried out as one combined step.

2. The method according to claim 1, further comprising:
   (e) optionally separating the organic phase from the aqueous phase, and isolating or purifying the nucleic acids from the aqueous phase.

3. The method according to claim 2, wherein the step of isolating and/or purifying the nucleic acid comprised in the aqueous phase according to step (f) is carried out by means of at least chromatographic and/or solid phase-based method.

4. The method according to claim 3, wherein the at least chromatographic and/or solid phase-based method is selected from the group consisting of gel filtration chromatography, ion exchange chromatography, reversed phase chromatography, and chaotrope-free affinity binding.

5. The method according to claim 3, wherein the lysis buffer comprises an anionic surfactant ion, and wherein after incubation according to step (d), the anionic surfactant ion is essentially removed from the sample by precipitation using monovalent ions of alkali metals and/or divalent ions of alkaline earth metals prior to isolating and/or purifying the nucleic acid from the aqueous phase.

6. The method according to claim 5, wherein the monovalent ions of alkali metals and/or divalent ions of alkaline earth metals are selected from the group consisting of $Rb^+$, $Cs^+$, $Ca^{2+}$, $Sr^{2+}$, $Ba^{2+}$, and a mixture thereof.

7. The method according to claim 5, wherein isolating and/or purifying the nucleic acid from the aqueous phase is performed using gel filtration chromatography.

8. The method according to claim 1, wherein the sample is a paraffin embedded sample.

9. The method according to claim 8, wherein the paraffin embedded sample is a formalin-fixed paraffin-embedded sample (FFPE-sample).

10. The method according to claim 8, wherein the at least one organic solvent is selected from the group consisting of linear, branched and cyclic $C_{10}$-$C_{16}$ alkanes and mixtures thereof.

11. The method according to claim 8, wherein the at least one organic solvent comprises hexadecane.

12. The method according to claim 1, wherein a dye/a colorant may be comprised in the wax-solubilizing agent.

13. The method according to claim 1, wherein the method comprises step (b), and wherein the step of incubating the mixture of the wax-solubilizing agent and the wax-embedded sample according to step (b) is carried out at a temperature in the range of from 15° C. to 85° C.

14. The method according to claim 13, wherein the step of incubating the mixture of the wax-solubilizing agent and the wax-embedded sample according to step (b) is carried out at a temperature in the range of from 20° C. to 55° C.

15. The method according to claim 14, wherein the step of incubating the mixture of the wax-solubilizing agent and the wax-embedded sample according to step (b) is carried out at a temperature in the range of from room temperature to 35° C.

16. The method according to claim 15, wherein the step of incubating the mixture of the wax-solubilizing agent and the wax-embedded sample according to step (b) is carried out at room temperature.

17. The method according to claim 13, wherein the step of incubating the mixture of the wax-solubilizing agent and the wax-embedded sample according to step (b) is carried out at a temperature in the range of from 15° C. to 85° C. for 1 second to 3 hours, for 10 seconds to 1 hour, from 20 seconds to 30 minutes, or from 30 seconds to 15 minutes.

18. The method according to claim 1, wherein the lysis buffer comprises a buffering agent and a detergent.

19. The method according to claim 18, wherein the buffering agent is selected from the group consisting of Tris, Mops, Mes, Hepes, phosphates, borates and carbonates, and the detergent is selected from the group consisting of anionic and zwitterionic detergents.

20. The method according to claim 18, wherein the lysis buffer further comprises one or more substances selected from the group consisting of chelating agents, reducing agents, inorganic salts, pH indicators, and stabilizers.

21. The method according to claim 20, wherein the lysis buffer has a pH in the range of from 4 to 11, from 7 to 10, or from 8 to 9.

22. The method according to claim 1, wherein a proteolytic agent either is added to the mixture in step (c) in addition to the lysis buffer, or a proteolytic agent is already comprised in the lysis buffer added to the sample in step (c), said proteolytic agent being selected from the group consisting of proteases and non-enzymatic proteolytic compounds.

23. The method according to claim 22, wherein said proteolytic agent is selected from the group consisting of proteinase K, trypsin, chymotrypsin, papain, pepsin, pronase, endoproteinase Lys-C, bromocyane, recombinant *Bacillus* proteases, Lysozyme, and a mixture thereof.

24. The method according to claim 1, wherein the step of incubating the mixture obtained after adding the aqueous lysis buffer to the sample according to step (d) is carried out at a temperature in the range of from 15° C. to 95° C.

25. The method according to claim 24, wherein the step of incubating the mixture obtained after adding the aqueous lysis buffer to the sample according to step (d) is carried out at a temperature in the range of from 20° C. to 70° C.

26. The method according to claim 25, wherein the step of incubating the mixture obtained after adding the aqueous lysis buffer to the sample according to step (d) is carried out at a temperature in the range of from 37° C. to 65° C.

27. The method according to claim 1, wherein the step of incubating the mixture obtained after adding the aqueous lysis buffer to the sample according to step (d) is carried out at a temperature in the range of from 15° C. to 95° C. for 30 seconds to 24 hours, 50 seconds to 12 hours, 50 seconds to 5 hours, or 1 minute to 2 hours.

28. The method according to claim 1, wherein the nucleic acids are selected from the group consisting of ribonucleic acids (RNA) and desoxyribonucleic acids (DNA).

29. The method according to claim 1, wherein the nucleic acids are DNA.

30. The method according to claim 1, wherein the nucleic acids are DNA having a length of at least 100 bp.

* * * * *

UNITED STATES PATENT AND TRADEMARK OFFICE
CERTIFICATE OF CORRECTION

PATENT NO. : 9,458,494 B2
APPLICATION NO. : 13/703205
DATED : October 4, 2016
INVENTOR(S) : Markus Mueller et al.

Page 1 of 1

It is certified that error appears in the above-identified patent and that said Letters Patent is hereby corrected as shown below:

In the Claims

Column 20, Lines 16-19:
"2. The method according to claim 1, further comprising:
(e)      optionally separating the organic phase from the aqueous phase, and isolating or purifying the nucleic acids from the aqueous phase." should read,
--2. The method according to claim 1, further comprising:
(e)      optionally separating the organic phase from the aqueous phase, and
(f)      isolating or purifying the nucleic acids from the aqueous phase.--.

Signed and Sealed this
Thirtieth Day of May, 2017

Michelle K. Lee
*Director of the United States Patent and Trademark Office*